United States Patent [19]
Thornton et al.

[11] Patent Number: 5,741,320
[45] Date of Patent: Apr. 21, 1998

[54] CATHETER CONTROL SYSTEM HAVING A PULLEY

[75] Inventors: Peter Thornton, Los Altos; Tracy D. Maahs, San Jose; Robert C. Hayzelden, Canyon Lake; Miriam H. Taimisto, Anaheim Hills, all of Calif.

[73] Assignee: Heart Rhythm Technologies, Inc., Temecula, Calif.

[21] Appl. No.: 433,229

[22] Filed: May 2, 1995

[51] Int. Cl.$^6$ .................................................. A61M 37/00
[52] U.S. Cl. .................................................. 607/122; 604/95
[58] Field of Search ........................... 604/95, 264, 200, 604/202; 600/114, 131, 146, 149; 607/122

[56] References Cited

U.S. PATENT DOCUMENTS

| | | |
|---|---|---|
| Re. 34,502 | 1/1994 | Webster, Jr. . |
| 3,452,740 | 7/1969 | Muller . |
| 3,470,876 | 10/1969 | Barchilon . |
| 3,521,620 | 7/1970 | Cook . |
| 3,552,384 | 1/1971 | Pierie et al. . |
| 3,605,725 | 9/1971 | Bentov . |
| 3,610,231 | 10/1971 | Takahashi et al. . |
| 4,207,873 | 6/1980 | Kruy . |
| 4,483,326 | 11/1984 | Yamaka et al. . |
| 4,503,842 | 3/1985 | Takayama . |
| 4,898,577 | 2/1990 | Badger et al. . |
| 4,996,974 | 3/1991 | Ciarlei ................ 600/149 X |
| 5,030,204 | 7/1991 | Badger et al. . |
| 5,125,896 | 6/1992 | Hojeibane . |
| 5,170,787 | 12/1992 | Lindegren . |
| 5,181,514 | 1/1993 | Solomon et al. . |
| 5,185,004 | 2/1993 | Lashinski . |
| 5,190,050 | 3/1993 | Nitzsche . |
| 5,195,968 | 3/1993 | Lundquist et al. . |
| 5,228,441 | 7/1993 | Lundquist . |
| 5,242,430 | 9/1993 | Arenas et al. . |
| 5,242,441 | 9/1993 | Avitall . |
| 5,254,088 | 10/1993 | Lundquist et al. . |
| 5,255,668 | 10/1993 | Umeda . |
| 5,255,684 | 10/1993 | Rello . |
| 5,257,451 | 11/1993 | Edwards et al. . |
| 5,263,493 | 11/1993 | Avitall . |
| 5,273,535 | 12/1993 | Edwards et al. . |
| 5,281,217 | 1/1994 | Edwards et al. . |
| 5,284,128 | 2/1994 | Hart . |
| 5,318,525 | 6/1994 | West et al. . |
| 5,327,905 | 7/1994 | Avitall . |
| 5,330,466 | 7/1994 | Imran . |
| 5,346,504 | 9/1994 | Ortiz et al. . |
| 5,354,297 | 10/1994 | Avitall . |
| 5,358,479 | 10/1994 | Wilson . |
| 5,363,861 | 11/1994 | Edwards et al. . |

(List continued on next page.)

OTHER PUBLICATIONS

International Search Report for Application No. PCT/US96/06061 dated Jun. 24, 1996 (foreign counterpart to present application).

*Primary Examiner*—Mark Bockelman
*Assistant Examiner*—N. Kent Gring
*Attorney, Agent, or Firm*—Fulwider Patton Lee & Utecht, LLP

[57] ABSTRACT

A steerable catheter comprising a resilient body member, a manipulation handle attached to the proximal end of the body member, a control wire extending from the handle to the distal end of the catheter for deflection control, and a pulley mechanism for controlling the movement of the control wire. Longitudinal movement of a slide element in the handle causes movement of the control wire and control over the deflection of the distal end of the catheter. The pulley mechanism is connected between the slide element and the control wire to provide greater mechanical advantage to effect deflection of the body member while enhancing deflection control resolution. A stiffening member is also disposed in the catheter body member and its position is controlled by the rotational motion of the slide element. The position of the pulley mechanism is not affected by rotational motion of the slide element.

41 Claims, 3 Drawing Sheets

U.S. PATENT DOCUMENTS

| | | |
|---|---|---|
| 5,368,564 | 11/1994 | Savage . |
| 5,370,678 | 12/1994 | Edwards et al. . |
| 5,383,852 | 1/1995 | Stevens-Wright . |
| 5,383,923 | 1/1995 | Webster, Jr. . |
| 5,385,148 | 1/1995 | Lesh et al. . |
| 5,395,327 | 3/1995 | Lundquist et al. . |
| 5,402,793 | 4/1995 | Gruner et al. . |
| 5,403,297 | 4/1995 | Imran . |
| 5,431,168 | 7/1995 | Webster, Jr. . |
| 5,441,483 | 8/1995 | Avitall . |
| 5,465,716 | 11/1995 | Avitall . |
| 5,471,982 | 12/1995 | Edwards et al. . |
| 5,476,495 | 12/1995 | Schoenborn . |

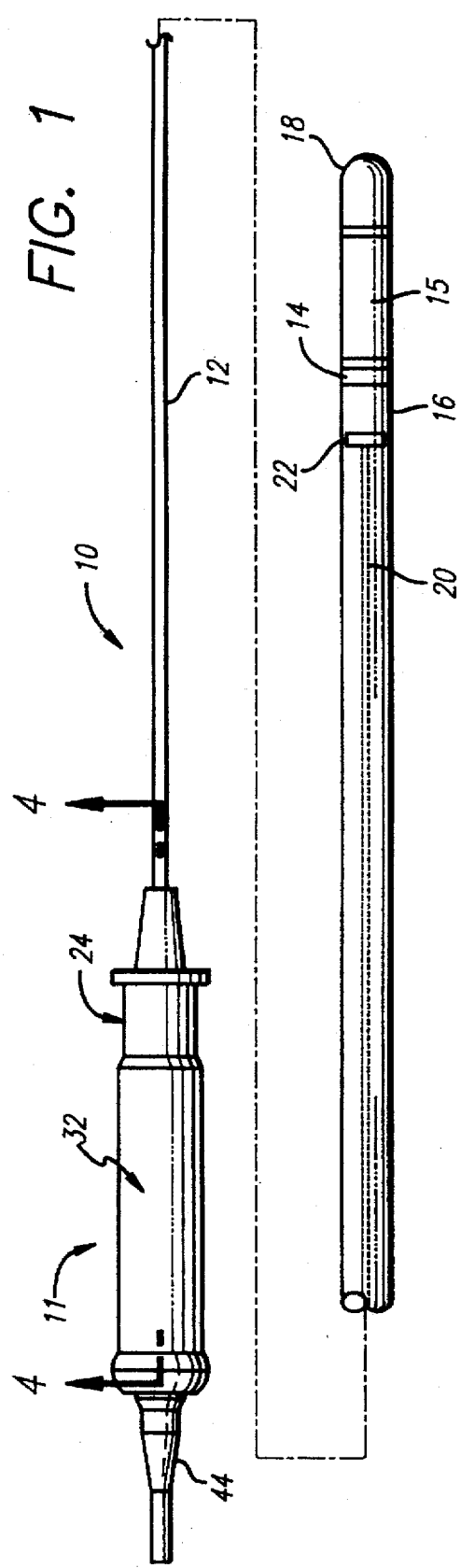
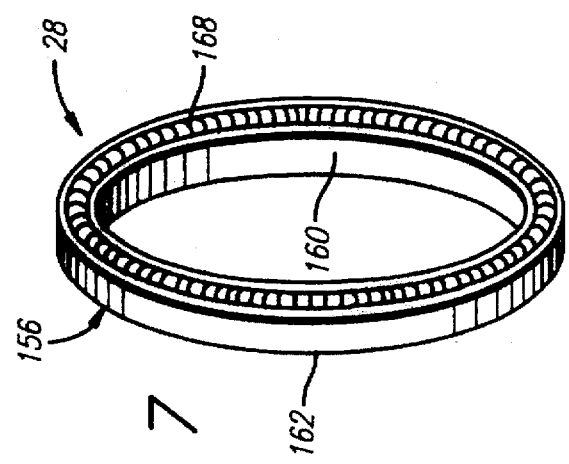
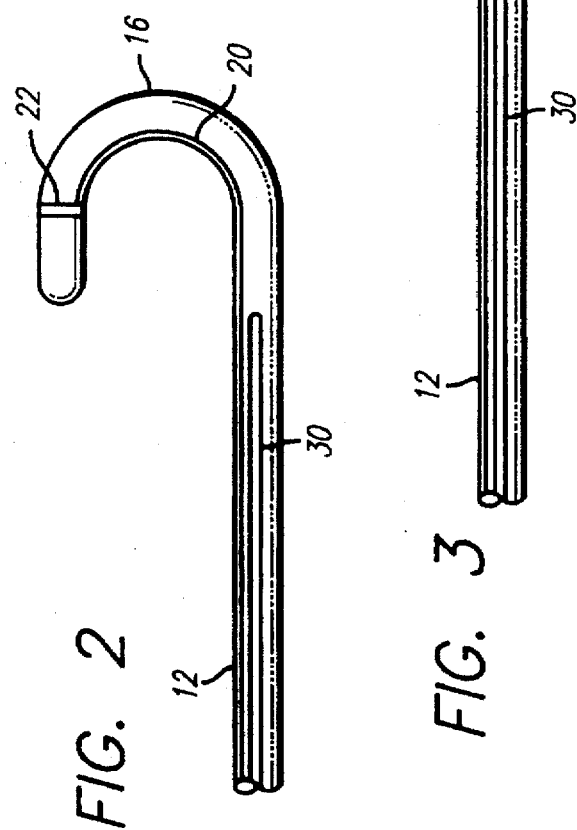

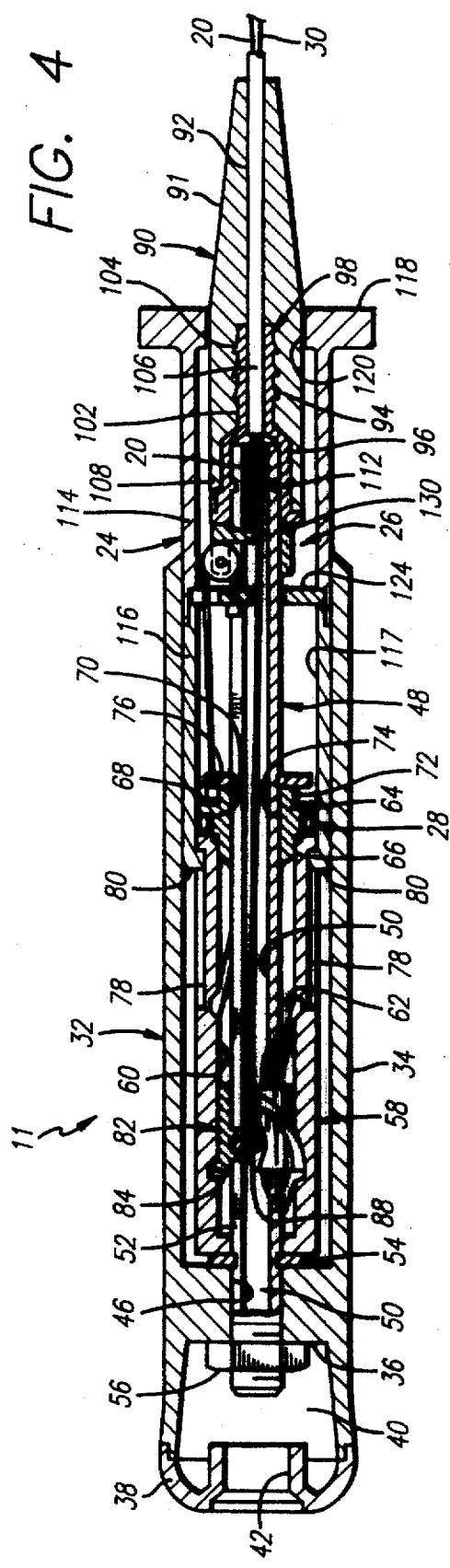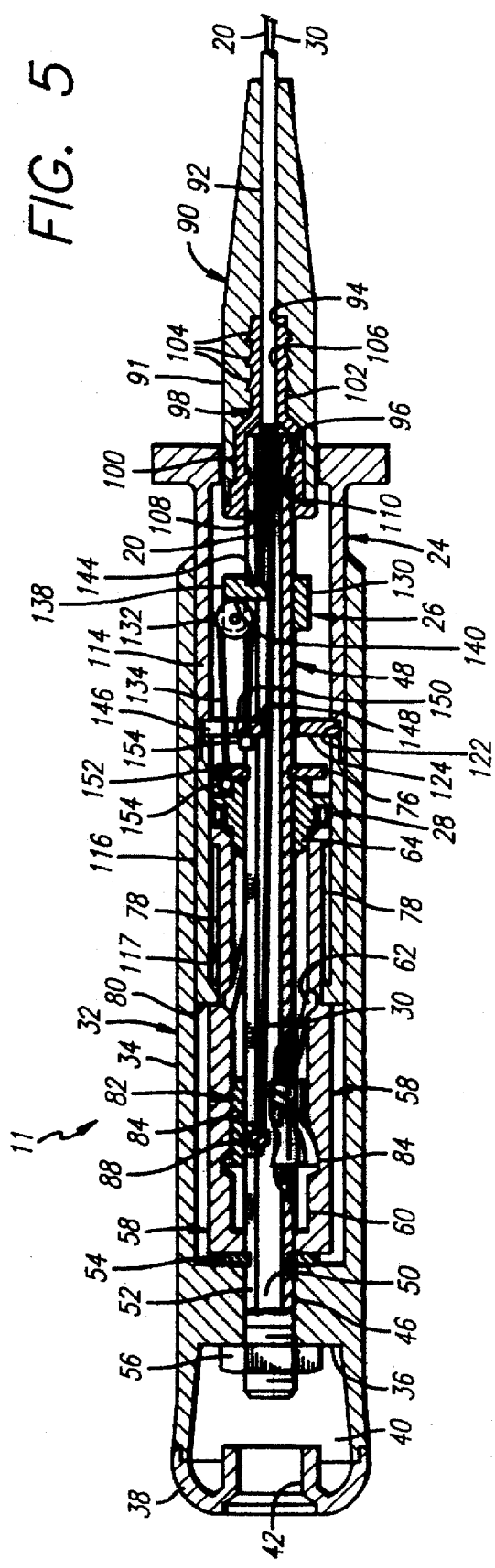

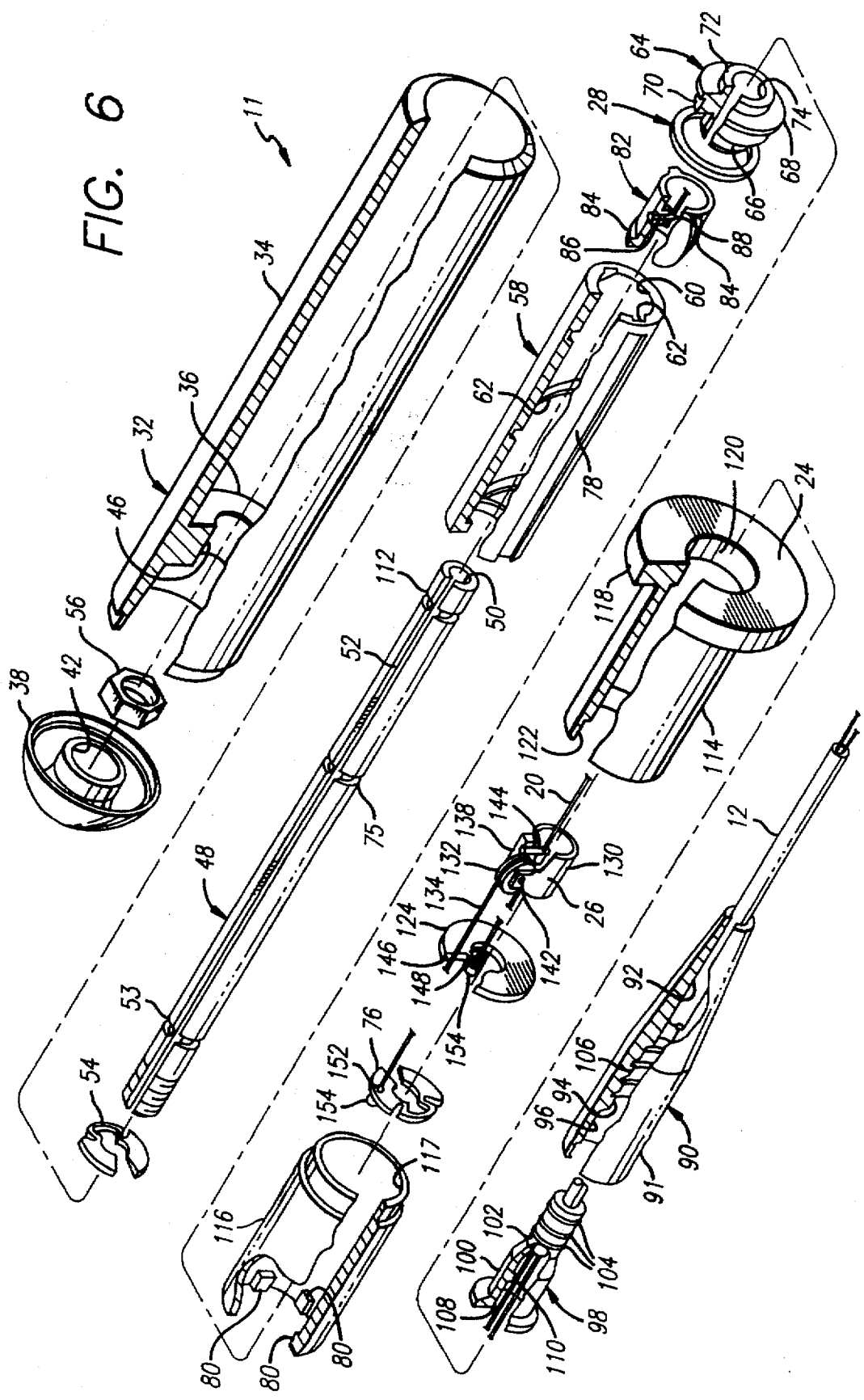

CATHETER CONTROL SYSTEM HAVING A PULLEY

BACKGROUND

The invention relates generally to steerable catheters, and more particularly, to control systems included in a catheter for providing greater control over the deflection of a catheter's distal end.

The heart beat in a healthy human is controlled by the sinoatrial node ("S-A node") located in the wall of the right atrium. The S-A node generates electrical signal potentials that are transmitted through pathways of conductive heart tissue in the atrium to the atrioventricular node ("A-V node") which in turn transmits the electrical signals throughout the ventricle by means of the His and Purkinje conductive tissues. Improper growth of or damage to the conductive tissue in the heart can interfere with the passage of regular electrical signals from the S-A and A-V nodes. Electrical signal irregularities resulting from such interference can disturb the normal rhythm of the heart and cause an abnormal rhythmic condition referred to as cardiac arrhythmia.

Electrophysiological ablation is a procedure often successful in terminating cardiac arrhythmia. This procedure involves applying sufficient energy to the interfering tissue to ablate that tissue thus removing the irregular signal pathway. However, before an ablation procedure can be carried out, the interfering tissue must first be located.

One location technique involves an electrophysiological mapping procedure whereby the electrical signals emanating from the conductive endocardial tissues are systematically monitored and a map is created of those signals. By analyzing that map, the interfering electrical pathway can be identified. A conventional method for mapping the electrical signals from conductive heart tissue is to percutaneously introduce an electrophysiology ("EP") catheter having mapping electrodes mounted on its distal extremity. The catheter is maneuvered to place those electrodes in contact with or in close proximity to the endocardium of the patient's heart. By monitoring the electrical signals at the endocardium, aberrant conductive tissue sites responsible for the arrhythmia can be pinpointed.

Once the origination point for the arrhythmia is located in the tissue, the physician may use an ablation procedure to destroy the tissue causing the arrhythmia in an attempt to remove the electrical signal irregularities and restore normal heart beat or at least improve the heart beat. Successful ablation of the conductive tissue at the arrhythmia initiation site usually terminates the arrhythmia or at least moderates the heart rhythm to acceptable levels.

In order to perform the above described electrophysiological procedures, the EP catheter, having mapping and ablation electrodes at the distal end thereof, is percutaneously introduced into the cardiovascular system of the patient through a blood vessel, for instance the femoral artery, and advanced to a selected endocardial site in the atrium or ventricle. Once the EP catheter has reached the heart, it must be maneuvered to place its electrodes or other active devices in the required positions to perform the EP procedures.

A steerable catheter may be used that has an internal deflection control line attached at a point adjacent the distal tip of the catheter. Pulling the proximal end of the control line at the manipulation handle causes the distal tip of the catheter to bend in one direction so that the tip may be directed to a selected endocardial site. The ability to position the devices at the distal end of the catheter in relation to the target site is important to obtaining good results. The deflection of the distal portion of the catheter may have to be finely adjusted to orient it properly for comprehensive monitoring of the electrical signals emanating from the conductive heart tissue for effective mapping and detection of arrhythmatic points of origin. In some cases, minute changes in deflection are required to position the distal end of the catheter properly. Minute changes in distal end deflection may also be required in the ablation process.

Hence, those skilled in the art have recognized that it would be desirable for a steerable catheter to include a deflection control mechanism that decreases the amount of force required of the operator of the manipulation handle to achieve the desired deflection of the distal end of the catheter. Reducing the amount of force required to achieve deflection will result in greater control and comfort thus reducing physician fatigue. Additionally, it has been recognized that it would be desirable for a steerable catheter to include a deflection control mechanism that increased the resolution of deflection of the distal end with movement of the manipulation handle. Such increased resolution should provide increased positioning and control to allow for fine catheter distal end adjustments. Furthermore, the manipulation handle and control mechanism of the catheter should be relatively easy to operate, relatively inexpensive to manufacture, and reliable in use. The present invention fulfills these needs and others.

SUMMARY OF THE INVENTION

Briefly and in general terms, the present invention is directed to a catheter having a movable member, the position of which is controlled at the proximal end of the catheter by means including a pulley. A manipulation handle at the proximal end of the catheter controls the position of the movable member through the use of the pulley mechanism to achieve greater resolution and decreased force required for positioning the movable member. In one aspect, the movable member is used to control the deflection of the distal tip of the catheter and the pulley mechanism coupled to the movable member and the handle reduces the amount of force required on the handle to deflect the distal tip while at the same time resulting in greater resolution of the amount of deflection. The use of the pulley mechanism increases the mechanical advantage of forces applied at the proximal end of the catheter to effect distal tip deflection of the catheter while enhancing control resolution.

In a more detailed aspect, the pulley mechanism is incorporated in a steerable catheter including a resilient body member having distal and proximal ends with a manipulation handle attached to the proximal end of the body member. A deflection control line is attached at the distal end of the catheter to control deflection of the tip. Movement of the control line axially in the catheter body member results in more or less deflection of the distal tip. The proximal end of the control line is attached to a pulley mechanism within the manipulation handle. The handle has first and second elements movable in relation to each other, and such movement results in control over the axial movement of the control line through the pulley mechanism.

In a more detailed aspect, the pulley mechanism includes a pulley bracket mounted in the manipulation handle that is movable in relation to the first and second elements of the handle. A pulley is rotatably mounted to the pulley bracket and a pulley cable is engaged with the pulley. The pulley cable has first and second ends, the first end being affixed to either the first or second element of the handle and the second end of the cable is affixed to the other element.

In a more particular aspect, the first element of the handle includes a hand grip and is stationary relative to the second element and the pulley bracket. The second element is slidable and in another aspect, is additionally rotatable, inside the first element. The pulley bracket is non-rotatable relative to the hand grip. In particular, a shaft is mounted inside the first element, the shaft having a longitudinal slot and the pulley bracket is configured to engage the slot to restrain rotational movement of the pulley bracket relative to the shaft and first element.

In operation, movement of the first and second elements in relation to each other results in movement of one end of the pulley cable thereby causing the pulley bracket to move the control wire in the distal end of the body member. Such movement causes deflection of the distal end of the body member. The use of the pulley mechanism described above results in greater mechanical advantage of movement of the first and second elements in relation to each other while providing the user with increased control resolution over the position of the control line and hence, the deflection of the distal tip.

Other aspects and advantages of the invention will become apparent from the following detailed description and accompanying drawings, illustrating by way of example the features of the invention.

BRIEF DESCRIPTION OF THE DRAWINGS

FIG. 1 is a side view of an electrophysiological catheter embodying features of the invention, having a manipulation handle with a male connector and cable connected thereto, an elongated shaft with an internal control line, and showing the distal end enlarged;

FIG. 2 is a schematic side view of the distal portion of the catheter shown in FIG. 1 with tension applied to the internal control line that extends into and is anchored to the distal portion of the catheter to cause a deflection of the distal end;

FIG. 3 is a schematic side view of a distal portion of the catheter similar to that shown in FIG. 2, except that in addition to tension being applied to the control line, a stiffening member is advanced into the distal portion of the catheter thereby controlling the stiffness and the deflected shape of the distal end of the catheter;

FIG. 4 is a side view, partially in section, of the manipulation handle shown in FIG. 1 secured to the proximal end of the catheter taken along line 4—4 of FIG. 1 without the connector and cable in place, and including a pulley mechanism in accordance with principles of the invention;

FIG. 5 is a side view, partially in section, of the manipulation handle shown in FIG. 4, but illustrating a slide element of the handle moved in a proximal direction relative to its position shown in FIG. 4;

FIG. 6 is an exploded perspective view, partially in section, of the manipulation handle shown in FIGS. 4 and 5; and FIG. 7 is an enlarged perspective view of a locking device used to lock the position of the slide element on the handle.

DETAILED DESCRIPTION OF THE PREFERRED EMBODIMENTS

Referring now to the drawings in which like reference numerals designate like or corresponding elements among the several views, there is shown in FIG. 1 a catheter 10 usable for electrophysiological procedures and embodying features of the invention. Briefly, the catheter 10 includes a manipulation handle 11 attached to the proximal end of an elongated catheter shaft or body member 12. The catheter 10 includes a plurality of sensing electrodes 14 and 18 at the distal end 16 thereof. The distal tip electrode 18 may also function as an ablation electrode. The sensing electrodes 14 and 18 are connected to electrical conductors that extend through the body member 12, through the handle 11, to a receptacle 43 (not shown) internal to the handle 11. Connected to that receptacle or female connector 43 is an external male connector 44 to conduct signals developed by the catheter 10 to external equipment and to provide ablation energy to the catheter.

The conductors are mounted in an inner lumen (not shown) of the body member 12. Although four sensing electrodes 14 and 18 are shown in FIG. 1, more or fewer of these electrodes may be used depending on the application. Additionally, the types of devices and their locations mentioned above and shown in the figures are only for purposes of illustration. Other types of devices and locations may be used. For example, an ultrasonic device may be used for ablation and may take the form of a side-fire device or an end-fire device. Additionally, different types of connectors may be used at the proximal end of the handle 11. Instead of a female connector in the handle, a male connector may be used to mate with an external connector, depending on the application.

A movable catheter control device is disposed within the catheter body member 12 and in this embodiment, comprises a deflection control line 20. The control line 20 has its distal end located at the distal end 16 of the body member 12 and is anchored there by attachment to a stationary anchor band 22. The distal end of the deflection control line 20 is secured by brazing, soldering or by similar means to the anchor band 22. In an alternative embodiment, the control line may be secured to one of the electrodes by similar means, instead of an additional anchor plate. The deflection control line 20 in this embodiment has a lubricous outer coating or jacket (not shown) and is placed in an inner lumen of the body member 12. That lumen is offset from the central longitudinal axis of the catheter body member 12 to more easily effect the deflection of the flexible distal end 16.

Longitudinal movement of the control line 20 in the proximal direction causes deflection of the distal end 16 of the body member. The body member 12 is typically fabricated of a flexible resilient material and is constructed so that it tends to assume a particular shape when at rest. When a deflection force is imparted to the distal end of the body member to achieve deflection, such as the deflection shown in FIG. 2, the inherent construction of the body member exerts an opposing, restoring force (in this case a straightening force) that tends to return the body member to its "at rest" shape. In the case of FIG. 1, the body member assumes a straight shape when at rest. When enough tension is applied to the control line 20, deflection occurs but the body member applies an opposing straightening force. When all deflection forces have been removed from the distal end, this force created by the construction of the body member returns the body member to a straightened position. Thus, enough tension must be applied to the deflection control line 20 to counteract the body member's restoring force so that deflection of the distal end can occur.

At its proximal end, the control line 20 is connected to an element in the handle 11. The handle includes a body portion 32 and one or more elements movable in relation to the body portion 32. When the element to which the control line 20 is attached is moved in the proximal direction in relation to the handle body portion, tension is applied to the deflection control line 20 and deflection of the distal end of the catheter body results. The distal end will be deflected from the rest position shown in FIG. 1 to a curved shape such as that shown in FIGS. 2 or 3. The amount of tension applied to the control line by the handle element determines the amount of deflection of the distal end of the catheter, within certain limits.

With particular reference to FIGS. 2 and 3, the catheter 10 of this embodiment also includes a mandrel or stiffening member 30 slidably disposed within an inner lumen of the body member 12. The advancement and retraction of the stiffening member 30 within the distal end 16 of the catheter body member 12 controls the stiffness of the distal end and in conjunction with the deflection control line 20, allows greater control over the shape of the flexible distal end when deflected.

In FIG. 2, the stiffening member 30 is shown substantially withdrawn from the distal end 16 of the catheter body member 12 so that tension applied to the deflection control line 20 will result in a curvature of the distal end 16 as shown. As depicted in FIG. 3, the stiffening member 30 has been advanced into the distal end 16 of the body member 12, wherein the curvature of the body member is correspondingly altered from that shown in FIG. 2. Cooperation of the stiffening member 30 and the control line 20 allows for selective variability of the distal end radii of curvature resulting in increased capabilities for body member steering and distal end intracardial placement. The stiffening member also increases the stiffness so that greater pressure can be applied to the target tissue, increasing the catheter's ability to remain in place after a site has been selected.

The deflection control line 20 and stiffening member 30 are preferably formed of a stainless steel suitable for in vivo use, although other materials may be used. In one embodiment, the deflection control line 20 was about 0.127 to about 0.254 mm (0.005 to 0.010 inch) in diameter and the stiffening member 30 was about 0.254 to 0.508 mm (0.010 to about 0.020 inch) in diameter, and the lengths thereof are appropriate for the catheter in which they are utilized. The sizes of the above elements would be adjusted for catheters of different sizes.

Referring now to FIGS. 4, 5, and 6, the manipulation handle 11 will be described in detail. The handle 11 includes an elongated, hollow, generally cylindrical, handle body 32 having a partition wall 36 near the proximal end thereof and a contoured cap 38 affixed to the proximal end of the handle body that encloses a hollow proximal cavity 40. The contoured cap 38 includes an axial connector bore 42 for receiving an electrical female receptacle 43. For purposes of convenience, the female receptacle will be referred to as a connector.

The partition wall 36 of the handle body 32 has an axial bore 46 for receipt of a tubular shaft 48. The shaft has a circumferential groove 53 (more clearly shown in FIG. 6) near its proximal end for receiving a spring clip 54. The proximal extremity of the shaft is threaded and is received within the bore 46 of the partition wall 36 and extends rearwardly therefrom so that a nut 56 can be threaded onto the proximal end of the shaft. Tightening the nut secures the shaft in position at the partition wall with the spring clip 54 on one side and the nut on the other. Thus, the shaft 48 is anchored in position in the handle body. The nut may be secured in position by the use of a thread locking adhesive or a lock washer (not shown), or other means.

A strain relief 90 is fixedly secured to the distal end of an anchor cap 98. The distal end of the strain relief is formed with an axial catheter tube bore 92 stepping proximally to a larger diameter medial bore 94 and tapering therefrom to a once again larger diameter proximal bore 96 extending to the proximal extremity of the strain relief. The medial bore and proximal bore are sized for complementary receipt of the distal handle anchor cap 98.

The distal anchor device 98 has a stem 102 having a plurality of annular barbs 104 formed about the periphery thereof for mating with the strain relief 90. The stem of the distal anchor device has a catheter anchor bore 106 sized for receipt of the catheter tube 12. The bore tapers proximally to a larger diameter bore 108 for mating with the distal end of the tubular shaft 48. The proximal end of the catheter tube 12 is received in the distal catheter tube bore 92 and anchor bore 106, and affixed therein by a suitable adhesive. The shaft bore 108 of the distal anchor device 98 is slidably disposed over the distal end of the tubular shaft 48. The distal anchor device 98 is secured by a suitable adhesive to the shaft 48 so that the strain relief 90 is thereby also affixed to the distal end of the tubular shaft 48.

Electrical sensing and ablation conductors (not shown) lead from the distal end of the catheter body member 12, pass through the inner lumen 50 of the tubular shaft 48, and are electrically connected to the electrical connector 43.

With continued reference to FIGS. 4, 5, and 6, a slide element 24 is constructed of a generally tubular distal sleeve element 114 and a tubular proximal sleeve element 116, the proximal sleeve element having an axial bore 117 therethrough. The tubular walls of the respective sleeve elements are of substantially the same radial thickness. The outer diameters of the respective sleeve elements are sized for slidable receipt within the handle body 32. The distal end of the distal sleeve element 114 is formed with an enlarged knob 118 configured for convenient grasping by the physician and the inner portion of the distal end of the distal sleeve element is formed with a smaller diameter collar 120 for slidable receipt of the cylindrical portion 91 of the strain relief 90. The proximal extremity of the distal sleeve element 114 is formed with a counterbore 122 or threading in its proximal end. The distal end of the proximal sleeve element 116 has a mounting flange sized to fit within the counterbore 122 of the distal sleeve element 114. In an alternative embodiment, it may have threads for threading into the threaded area of the distal sleeve element 114. A ring 124 is mounted in the counterbore 122 and then the mounting flange is placed into the counterbore to capture the ring 124. When so joined, the sleeve elements form a substantially continuous cylindrical slide element 24, wherein the ring 124 is held in position axially between the elements and the elements can rotate around the ring 124.

A pulley mechanism 26 will now be described in detail. The pulley mechanism cooperates with the slide element 24 to effectuate control movements of the deflection control line 20. The pulley mechanism includes a pulley bracket 130 in which is mounted a pulley 132 that engages a pulley cable 134. The pulley bracket is generally cylindrical having an axial bore 136 for mounting the bracket 130 over the tubular shaft 48 of the handle body 32. The pulley bracket 130 is mounted on the shaft 48 between the ring 124 of the slide element 24 and the distal anchor device 98. The pulley bracket includes a projecting ridge 138 having a slot 140 in which the pulley 132 is rotatably mounted on a transverse axle pin 142. The pulley bracket also includes an inwardly projecting tang 144 disposed distal of the pulley. In another embodiment, the pulley bracket 130 is cylindrical with an inwardly projecting pin. The proximal end of the deflection control line 20 is secured thereto by means such as soldering, brazing, or other. The pulley bracket is slidably disposed over the tubular shaft 48 so that the tang 144 and a portion of the pulley 132 are received within a longitudinal slot 52 in the shaft. As such, the pulley bracket is free to slide longitudinally over the shaft; however, confrontation of the tang or pin and the slot 52 constrains the pulley bracket from rotating relative to the shaft.

The ring 124 of the pulley mechanism 26 includes a radial slot 146 extending from the circumference of the ring inwardly. Inwardly disposed from the slot is a radial inward projection 148 (FIG. 6) sized for receipt within the longitudinal slot 52 of the tubular shaft 48, the projection 148 includes a small axial bore 150 therethrough. A female element spring clip 76 is disposed at a fixed position on the shaft and is also formed with a small bore 152 offset from the center of the clip. The respective bores 150 and 152 are sized for receipt of opposite ends of the pulley cable 134. The pulley cable 134 includes a pair of enlarged beads 154 or ferrules affixed to the opposite ends thereof and are larger than the pulley cable and bores 150 and 152. One end of the pulley cable is disposed within the bore 152 of the spring clip 76. The pulley cable is received within the slot 146 of the ring 124 and wrapped around the pulley 132. The other end of the pulley cable is received within the bore 150 of the inward projection 148 of the ring 124. Because of the tang 144 of the pulley bracket and the projection 148 of the ring 124 located in the longitudinal slot of the shaft 48, the pulley mechanism is constrained from rotational movement relative to the shaft 48 so that the pulley cable 134 does not twist. The pulley cable is maintained in a taut state as tension from the deflection control line 20 pulls on the tang 144 of the pulley bracket 130 due to the tendency of the catheter body to straighten, urging the pulley in a distal direction.

Longitudinal sliding movement of the slide element 24 in the proximal axial direction relative to the handle body 32 moves the ring 124 of the pulley mechanism 26 longitudinally in the proximal axial direction. Because one end of the pulley cable 134 is secured to the inward projection 148 of the ring 124 and the pulley cable is engaged to the pulley 132, the pulley bracket 130 and the deflection control line 20 also move in a proximal axial direction, but at one half the displacement of the ring 124. Conversely, longitudinal movement of the slide element 24 in the distal direction lessens the tension applied to the deflection control line 20 tending to allow the distal end 16 of the catheter body member to return to its normal straightened shape. As the catheter is returning, the deflection control line 20 pulls the pulley bracket in the distal direction.

When the pulley mechanism 26 is in an equilibrium state, the tensile straightening or restoring forces of the catheter tube are transmitted along the deflection control line 20 to the pulley bracket 130. From the pulley bracket, the forces are transferred to the pulley 132 and cable 134. The forces are then equally distributed to the two ends of the cable; one-half of the tensile force to each cable end. When selecting a different distal end deflection, the work energy required to pull the deflection control line 20 to a new position is the product of the magnitude of the tensile force exerted on the pulley bracket 130 to move the control line and the distance through which the pulley bracket 130 moves the control line. Therefore, when the pulley bracket is moved a distance X to attain a desired distal end deflection, a particular unit of work energy is expended. Because one end of the cable is fixed to the spring clip 76 of the handle body 32 and the other end of the cable fixed to the ring 124 of the slide element, when the slide element is displaced a longitudinal distance 2X, the pulley bracket is displaced only the distance X. Because the work energy required to move the pulley bracket the distance X remains constant and because the slide element must move twice the distance to move the pulley bracket that distance, only one-half the force is required to pull the slide element and effectively pull the pulley bracket and control line to deflect the distal tip of the catheter.

Once the catheter 10 has been directed through the blood vessels to the heart, the deflection and position of the distal portion of the catheter may have to be finely adjusted to facilitate complete comprehensive monitoring of the electrical signals emanating from the conductive heart tissue for effective mapping and detection of arrhythmatic points of origin. Because the slide element 24 moves twice the distance relative to the pulley bracket 130 to achieve selected catheter distal end deflections, the physician has twice the displacement resolution to control distal end deflection. Consequently, fine distal end deflection adjustments may be more readily controlled.

Also shown in FIGS. 2 through 6 is a stiffening member 30 that controls the shape of the distal end of the catheter. As shown in FIGS. 2 and 3, its longitudinal position controls the deflected shape. The stiffening member is attached to a movable element in the handle, and movement of that element causes longitudinal advancement or retraction of the stiffening member. In this embodiment, the stiffening member 30 is attached to the slide element so that rotation of the slide element causes longitudinal movement of the stiffening member 30.

Referring now in more detail to FIGS. 4, 5, and 6, the stiffening member 30 is passed through the inner lumen 50 of the shaft 48 and is secured at its proximal end to the tang 88 on the screw element 82 by suitable means such as by ultrasonic welding, soldering, an adhesive, or other means. The hollow screw element 82 is received within the bore 60 of a nut element 58 and includes a pair of opposed projecting helical ridges 84 sized for complementary threaded engagement within the nut element helical grooves 62. As shown more clearly in FIG. 6, the screw element includes an inward projection 86. The screw element is disposed over the shaft 48 and the inward projection 86 of the screw element is received within the longitudinal slot 52 of the shaft so that rotation of the screw element 82 is constrained, while longitudinal movement of the screw element relative to the shaft 48 and nut element 58 is permitted as the nut element is rotated.

The distal end of the nut threaded element mounts a generally cylindrical bushing 64. The bushing 64 is formed with an axial bore 74 therethrough sized so that the bushing 64 can be mounted over the tubular shaft 48. A proximally projecting cylindrical boss 66 is sized for receipt within the distal end of the bore 60 of the nut element 58. The bushing has a larger diameter cylindrical portion 68 formed with a circumferential locking device groove 70 for receiving a locking device 28 therein. The bushing further includes a smaller diameter distally projecting cylindrical spacer 72.

The nut element 58 and bushing 64 are disposed over the tubular shaft 48 concentrically within the sleeve 34 of the handle body 32 so that the end of the nut element 58, opposite the bushing 64, abuts the spring clip 54 at the proximal end of the handle body 32. The medial portion of the shaft includes a retaining groove 75 (shown more clearly in FIG. 6), spaced a predetermined distance from the spring clip 54. The retaining groove 75 is sized for receipt of a nut element locking spring clip 76 abutting the spacer 72 of the bushing 64 to restrain the nut threaded element from longitudinal movement, while allowing rotational freedom thereof. The nut element 58 acts as a nut and is rotatable with respect to the handle body 32 as described below.

The nut element 58 is provided with a plurality of longitudinally extending guide tracks 78 on the exterior thereof which are adapted to slidably receive respective longitudinal splines 80 disposed on the interior surface of the slide element 24. Such splines are sized and equiangularly spaced apart for complementary receipt within the guide tracks 78 of the nut element 58. As so constructed, the slide element 24 may be rotated within the sleeve 34 of the handle body 32 and the respective splines engage the respective tracks to turn the nut element relative to the handle body 32. The spline and track configuration allows the slide element to independently move longitudinally within the sleeve 34 of the handle body, the splines guided within the guide tracks of the nut element.

A locking device 28 is disposed within the retaining groove 74 of the bushing 64 between the distal extremity of the nut element 58 and the larger diameter portion 68 of the bushing. With reference to FIG. 7, the locking device includes a contact member 156 that is U-shaped in cross section, having inner and outer arms 160 and 162, respectively, the open volume between the arms defining an annulus. The inner diameter of the locking device is smaller than the outer diameter of this portion of the bushing 68 so that the locking device cannot rotate on the bushing. The bushing and locking device rotate with the nut element 58 so the friction force of the locking device does not impede rotation of the nut element. By this arrangement, the rotational motion of the slide element is decoupled from the longitudinal motion. Disposed within the annulus of the U-shaped contact member is a biasing member, in this case, a resilient annular coil spring 168 in compression. The size and shape of the contact member and the spring are selected so that the radial outward spring force of the spring causes the outer arm 162 of the contact member 156 to tend to expand radially outwardly.

When assembled, the nut element 58 and the bushing 64 having the locking device 28 mounted thereon are received within the proximal sleeve element bore 117 of the slide element 24. The spring 168 of the locking device exerts an outward radial force to uniformly press the outer contact arm 162 of the contact member 156 against the slide element bore 117 to impart a continuous locking force thereto. The spring 168 of the locking device 28 is selected to have a radial outwardly directed biasing force that imparts a contact locking force between the contact member 156 and the slide element bore 117 greater than the tensile force of the deflection control line 20 at any position over the full range of deflection. Once a selected deflection of the distal end of the catheter has been attained by longitudinal movement of the slide element 24, the locking device maintains the control element in that position. The locking device 28 counters the restoring force of the catheter body member 12 and holds the slide element at the selected position relative to the handle 11 to maintain the selected catheter distal end 16 deflection. For further details concerning a locking device, see co-pending patent application entitled "Locking Mechanism For Catheters" by Smith filed this same day having docket no. 34709 and incorporated herein by reference.

It has been found that the screw connection between the screw element 82 that controls the position of the stiffening member and the nut element 58 that interfaces with the slide element 24 is sufficient to counter any forces applied to the stiffening element by the distal end of the catheter that may tend to cause the stiffening element to move one way or the other. Thus, the locking device 28 and the bushing 62 rotate with the nut element 58 therefore providing locking only for longitudinal movement of the slide element 24. The screw connection described above provides locking against rotational forces.

Referring to FIGS. 4 and 5, to control the stiffening member 30, the slide element 24 would be rotated relative to the handle body 32. As the slide element is rotated, the splines 80 of the slide element engage the tracks 78 of the nut element 58 to rotate the nut element, which in turn moves the screw element 82 longitudinally within the helical grooves 62 and along the tubular shaft 48. Because the stiffening member is connected to the inward projection 86 on the screw element, longitudinal movement of the screw element results in longitudinal movement of the stiffening member 30 within the catheter body member 12. The stiffening member 30 has sufficient column strength to communicate the thrust applied to the proximal end to the distal end thereof and otherwise stiffen the distal end 16 of the catheter body member 12 and control the distal end deflection.

From the foregoing, it can be appreciated that the invention provides a steerable catheter 10 having a manipulation handle 11 with a system that provides greater mechanical advantage and increased resolution over distal end deflections. The effort on the part of the physician required to cause deflection is reduced while resolution over the amount of deflection is increased. As a result, the physician can more accurately position the distal end at selected endocardial sites.

While the invention has been described herein in terms of certain embodiments, it is clear that the invention is susceptible to numerous modifications and adaptations within the ability of those skilled in the art and without the exercise of inventive faculty. Thus, it should be understood that various changes in form, detail and usage of the present invention may be made without departing from the spirit and scope of the invention.

What is claimed is:

1. A catheter having a deflectable distal tip, the catheter comprising:

a resilient body member having a distal end and a proximal end;

a manipulation handle attached to the proximal end of the body member having first and second elements movable in relation to each other;

a pulley bracket mounted in the handle and movable in relation to the first and second elements;

a pulley rotatably mounted to the pulley bracket;

a pulley cable engaged with the pulley having first and second ends, the first end of the cable affixed to the first element and the second end of the cable affixed to the second element;

a deflection control line mounted in the body member and connected at a proximal end to the pulley bracket and extending into and attached at the distal end of the body member; and whereby movement of the first and second elements in relation to each other results in movement of one end of the pulley cable to cause the pulley bracket to move the control line in the distal end of the body member causing deflection of the distal end of the body member with greater mechanical advantage.

2. The catheter of claim 1 wherein the pulley is positioned between the distal end of the handle and the second end of the pulley cable.

3. The catheter of claim 1 wherein the first element further comprises:
a hand grip and the first element is stationary relative to the second element and to the pulley bracket.

4. The catheter of claim 1 wherein the second element is slidable inside the first element.

5. The catheter of claim 4 further comprising:
a stiffness control member movable in the body member and controllable at its proximal end by interconnection with the second element of the manipulation handle;
wherein rotational movement of the second element controls the position of the stiffness control member;
wherein the pulley bracket is mounted so that it is limited to longitudinal motion and its position is controlled by the sliding movement of the second member.

6. The catheter of claim 1 wherein the manipulation handle further includes a shaft having distal and proximal ends, the proximal end of the shaft affixed to the manipulation handle and the pulley bracket is slidably mounted on the shaft.

7. The catheter of claim 6 wherein the bracket is non-rotatable relative to the shaft.

8. The catheter of claim 7 wherein the shaft includes a longitudinal slot and the pulley bracket is engaged with the slot to restrain rotational movement of the pulley bracket relative to the shaft.

9. A catheter having a deflectable distal tip, the catheter comprising:
a resilient body member having a distal end and a proximal end;
a manipulation handle attached to the proximal end of the body member having first and second elements movable in relation to each other;
a pulley bracket slidably mounted in the handle for movement in an axial direction relative to the first and second elements;
a pulley rotatably mounted to the pulley bracket;
a pulley cable engaged with the pulley having first and second ends, the first end of the cable affixed to the first element and the second end of the cable affixed to the second element;
a deflection control line mounted in the body member and connected at a proximal end to the pulley bracket and extending into and attached at the distal end of the body member; and
whereby movement of the first and second elements in relation to each other results in movement of one end of the pulley cable to cause the pulley bracket to move the control line in the distal end of the body member causing deflection of the distal end of the body member with greater mechanical advantage.

10. The catheter of claim 9 wherein the pulley is positioned between the distal end of the handle and the second end of the pulley cable.

11. The catheter of claim 9 wherein the first element further comprises:
a hand grip and the first element is stationary relative to the second element and to the pulley bracket.

12. The catheter of claim 9 wherein the second element is slidable and rotatable inside the first element.

13. The catheter of claim 9 further comprising:
a stiffness control member movable in the body member and controllable at its proximal end by interconnection with the second element of the manipulation handle;
wherein rotational movement of the second element controls the position of the stiffness control member;
wherein the pulley bracket is mounted so that it is limited to longitudinal motion and its position is controlled by the sliding movement of the second member.

14. The catheter of claim 13 further comprising means for decoupling the rotation movement of the second element from the sliding movement of the second element.

15. The catheter of claim 14 wherein the shaft includes a longitudinal slot and the pulley bracket is engaged with the slot to restrain rotational movement of the pulley bracket relative to the shaft.

16. The catheter of claim 9 wherein the manipulation handle further includes a shaft having distal and proximal ends, the proximal end of the shaft affixed to the manipulation handle and the pulley bracket is slidably mounted on the shaft.

17. A catheter, comprising:
a body member having a proximal end and a distal end;
a deflectable tip mounted on the distal end of the body member;
a manipulation handle mounted to the proximal end of the body member;
a deflection controller having a pulley mechanism mounted to the manipulation handle; and
a deflection control line mounted in and extending through the body member, the deflection control line having a distal end attached to the deflectable tip and a proximal end attached to the pulley mechanism such that movement of the deflection controller is transmitted to the deflection control line by the pulley mechanism resulting in movement of the deflection control line causing a deflection of the deflectable tip with greater mechanical advantage.

18. The catheter of claim 17, wherein:
the manipulation handle comprises a gripping surface and a shaft mounted so that the gripping surface and the shaft are stationary in relation to each other; and
the deflection controller comprises a second element connected to the pulley mechanism and movable in relation to the gripping surface and the shaft such that movement of the second element causes movement of the control line with greater mechanical advantage.

19. The catheter of claim 18, wherein the pulley mechanism comprises:
a bracket slidably mounted on the shaft and connected to the proximal end of the deflection control line; and
a cable engaging the bracket and having a first end affixed to the first element and a second end affixed to the second element.

20. The catheter of claim 19, wherein the cable engages a bearing surface formed on the bracket.

21. The catheter of claim 19, wherein:
the pulley mechanism further comprises a pulley mounted on the bracket; and
the cable engages the pulley.

22. The catheter of claim 19 wherein the bracket is non-rotatable relative to the shaft.

23. The catheter of claim 22 wherein the shaft includes a longitudinal slot and the bracket is engaged with the slot to restrain rotational movement of the bracket relative to the shaft.

24. The catheter of claim 19 further comprising:
a second control line movable in the body member and controllable at its proximal end by interconnection with the second element of the manipulation handle;
wherein rotational movement of the second element controls the position of the second control line; and wherein the bracket is mounted so that it is limited to longitudinal motion and its position is controlled by a sliding movement of the second element.

25. The catheter of claim 24 further comprising means for decoupling the rotational movement of the second element from the sliding movement of the second element.

26. The catheter of claim 25 wherein the means for decoupling comprises a sleeve slidably mounted within the gripping surface and attached to the second element and mounted on the shaft such that the sleeve and second element slide longitudinally along the shaft.

27. The catheter of claim 26 wherein the means for decoupling further comprises a hollow screw having a threaded exterior and a longitudinal bore sized to be slidably mounted on the shaft, the hollow screw having a mount for attaching the proximal end of the second control line thereto; and a second sleeve having a longitudinal bore sized to mount on the shaft and attached to the second element, the bore having grooves configured to threadedly engage the threaded exterior of the hollow screw, wherein rotational movement of the second element is converted by the second sleeve and hollow screw to cause the second control line to move in a linear direction.

28. The catheter of claim 27 wherein shaft includes a longitudinal slot and the hollow screw is engaged with the slot to restrain rotational movement of the hollow screw relative to the shaft.

29. A catheter comprising:

a body member having a proximal end and a distal end;

a manipulation handle mounted to the proximal end of the body member having a controller having a pulley mechanism; and a control line mounted in and extending through the body member, the control line having a distal end extending to the distal end of the body member and a proximal end attached to the pulley mechanism such that movement of the controller is transferred by the pulley mechanism to the control line resulting in movement of the control line.

30. The catheter of claim 29 wherein:

the manipulation handle comprises a first gripping member and a second gripping member with the second gripping member being movable in relation to the first gripping member;

wherein the pulley mechanism is connected to the second gripping member to transmit movement of the second gripping member to the control line.

31. The catheter of claim 30 wherein the pulley mechanism comprises:

a pulley mounted between the second gripping member and the control line, wherein the pulley transmits movement of the second gripping member to the control line with mechanical advantage.

32. The catheter of claim 31 wherein the manipulation handle further comprises:

a shaft rigidly mounted to the first gripping member;

a bracket slidably mounted on the shaft, connected to the pulley, and connected to the proximal end of the control line; and a pulley cable engaging the pulley and having a first end affixed to the first gripping element and a second end affixed to the second gripping element.

33. The catheter of claim 32 wherein the bracket is mounted to the shaft such that it is non-rotatable about the shaft.

34. The catheter of claim 33 wherein the shaft includes a longitudinal slot and the bracket is engaged with the slot to restrain rotational movement of the bracket relative to the shaft.

35. The catheter of claim 29 further comprising:

a second control line movable in the body member and controllable at its proximal end by interconnection with the controller;

wherein rotational movement of the controller controls the position of the second control line; and wherein the pulley mechanism is mounted so that it is limited to longitudinal motion and its position is controlled by a sliding movement of controller.

36. The catheter of claim 35 further comprising means for decoupling the rotational movement of the controller from the sliding movement of the controller.

37. A method of transmitting movement of a movable member located at a manipulation handle of a catheter to the distal end of the catheter through an elongated control device disposed through the length of the catheter body, comprising the steps of:

moving a first control member in relation to a second control member located in the manipulation handle;

coupling the movement of the first control member to move a pulley mechanism located at the manipulation handle;

coupling the movement of the pulley mechanism to the elongated control device to thereby transmit the movement of the first control member to the distal end of the catheter through the elongated control device.

38. The method of claim 37 wherein the step of coupling the movement of the first control member comprises the step of mounting a pulley to a bracket;

mounting the bracket to a shaft fixed in position in relation to the second control member;

attaching the proximal end of the elongated control device to the bracket; and engaging the pulley with a cable attached at a first end to the first control member and at a second end to the second control member.

39. The method of claim 38 wherein the step of mounting the bracket comprises the steps of:

providing a longitudinal slot in the shaft; and engaging the bracket with the slot to restrain rotational movement of the bracket relative to the shaft.

40. The method of claim 37 further comprising the steps of:

rotating the first control member in relation to the second control member;

coupling the rotational movement of the first control member to a second elongated control device to cause the second elongated control device to move in a linear direction to thereby transmit the rotational movement of the first control member to the distal end of the catheter through the second elongated control device.

41. The method of claim 40 further comprising the step of decoupling the movement of the first control member to move the pulley from the rotating movement of the first control member.

* * * * *